United States Patent [19]

Smith

[11] 4,130,591

[45] Dec. 19, 1978

[54] 2-DECARBOXY-2-HYDROXY-METHYL-13,14-DIDEHYDRO-16-PHENOXY PGF COMPOUNDS

[75] Inventor: Herman W. Smith, Kalamazoo, Mich.

[73] Assignee: The Upjohn Company, Kalamazoo, Mich.

[21] Appl. No.: 880,742

[22] Filed: Feb. 24, 1978

Related U.S. Application Data

[62] Division of Ser. No. 814,410, Jul. 11, 1977, which is a division of Ser. No. 708,752, Jul. 26, 1976, Pat. No. 4,058,564.

[51] Int. Cl.$^2$ ............................................. C07C 177/00
[52] U.S. Cl. ...................................... 568/645; 568/646
[58] Field of Search ................................... 260/613 D

[56] References Cited

U.S. PATENT DOCUMENTS

| | | | |
|---|---|---|---|
| 3,810,943 | 5/1974 | Jones et al. | 260/600 |
| 3,932,496 | 1/1976 | Jung | 260/514 D |
| 3,935,254 | 1/1976 | Gandolfe et al. | 260/514 D |
| 3,984,400 | 10/1976 | Egglev et al. | 260/468 D |

OTHER PUBLICATIONS

Fried et al., J. Med. Chem., vol. 16, No. 4, pp. 429–430 (1973).
Fried et al., Annals of the New York Academy of Sciences, 180:38 (1971).

*Primary Examiner*—Gerald A. Schwartz
*Attorney, Agent, or Firm*—Robert A. Armitage

[57] ABSTRACT

This invention comprises certain analogs of the prostaglandins in which the C-1 carboxyl is replaced by a primary alcohol and the double bond between C-13 and C-14 is replaced by a triple bond. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

66 Claims, No Drawings

2-DECARBOXY-2-HYDROXY-METHYL-13,14-DIDEHYDRO-16-PHENOXY PGF COMPOUNDS

The present application is a divisional application of Ser. No. 814,410, filed July 11, 1977, now pending, which application is a divisional application of Ser. No. 708,752, filed July 26, 1976, issued as U.S. Pat. No. 4,058,564 on Nov. 15, 1977.

The present invention relates to prostaglandin analogs for which the essential material constituting a disclosure therefor is incorporated by reference here from U.S. Pat. No. 4,058,564, issued Nov. 15, 1977.

I claim:

1. A prostaglandin analog of the formula

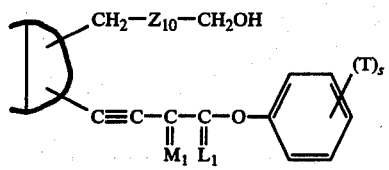

wherein ⟩ is

or

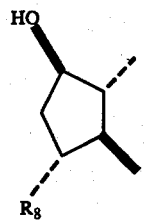

wherein $R_8$ is hydrogen or hydroxy;
wherein $M_1$ is

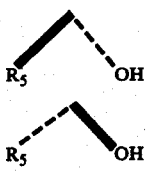

wherein $R_5$ is hydrogen or methyl;
wherein $L_1$ is

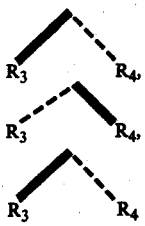

of a mixture of and

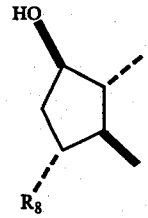

wherein $R_3$ and $R_4$ are hydrogen or methyl being the same or different;
wherein $Z_{10}$ is
(1) cis-$CH$=$CH$-$CH$-$(CH_2)_g$-$CH_2$—,
(2) cis-$CH$=$CH$-$CH_2$-$(CH_2)_g$-$CF_2$—,
(3) cis-$CH_2$-$CH$=$CH$-$(CH_2)_g$-$CH_2$—,
(4) —$(CH_2)_3$-$(CH_2)_g$-$CH_2$,
(5) —$(CH_2)_3$-$(CH_2)_g$-$CF_2$—, or
(6) —$CH_2$-$O$-$CH_2$-$(CH_2)_g$-$CH_2$—,
wherein g is one, 2, or 3; and
wherein s is one to 3, inclusive and T is chloro, fluoro, trifluoromethyl, alkyl of one to 3 carbon atoms, inclusive, or alkoxy of one to 3 carbon atoms, inclusive, the various T's being the same or different, with the proviso that not more than two are other than alkyl, with the further proviso that $Z_3$ is oxa only when $R_3$ and $R_4$ are hydrogen or methyl, being the same or different.

2. A prostaglandin analog according to claim 1, wherein ⟩ is

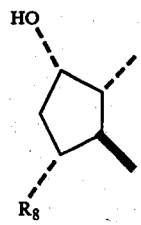

A prostaglandin analog according to claim 2, wherein R 3. is hydrogen.

4. A prostaglandin analog according to claim 2, wherein $R_8$ is hydroxy.

5. A prostaglandin analog according to claim 1, wherein   is

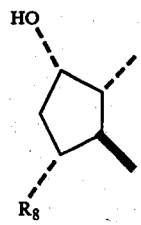

6. A prostaglandin analog according to claim 5, wherein $Z_{10}$ is cis—$CH$=$CH$-$CH_2$-$(CH_2)_g$-$CF_2$—.

7. 2-Decarboxy-2-hydroxymethyl-2,2-difluoro-13,14-didehydro-16-phenoxy-17,18,19,20-tetranor-$PGF_{2\alpha}$, a prostaglandin analog according to claim 6.

8. A prostaglandin analog according to claim 5, wherein $Z_{10}$ is —$(CH_2)_3$-$(CH_2)_g$-$CF_2$—.

9. 2-Decarboxy-2-hydroxymethyl-2,2-difluoro-13,14-didehydro-16-phenoxy-17,18,19,20-tetranor-$PGF_{1\alpha}$, a prostaglandin analog according to claim 8.

10. A prostaglandin analog according to claim 5, wherein $Z_{10}$ is cis-$CH_2$-$CH$=$CH$-$(CH_2)_g$-$CH_2$—.

11. 2-Decarboxy-2-hydroxymethyl-cis-4,5-didehydro-13,14-didehydro-16-phenoxy-17,18,19,20-tetranor-$PGF_{1\alpha}$, a prostaglandin analog according to claim 10.

12. A prostaglandin analog according to claim 5, wherein $Z_{10}$ is —$CH_2$-O-$CH_2$-$(CH_2)_g$-$CH_2$—.

13. 2-Decarboxy-2-hydroxymethyl-5-oxa-13,14-didehydro-16-phenoxy-17,18,19,20-tetranor-$PGF_1\alpha$, a prostaglandin analog according to claim 12.

14. A prostaglandin analog according to claim 5, wherein $Z_{10}$ is —$(CH_2)_3$—$(CH_2)_g$—$CH_2$—.

15. A prostaglandin analog according to claim 14, wherein $M_1$ is

16. 2-Decarboxy-2-hydroxymethyl-15-epi-13,14-didehydro-16-phenoxy-17,18,19,20-tetranor-$PGF_1\alpha$, a prostaglandin analog according to claim 15.

17. A prostaglandin analog according to claim 14, wherein $M_1$ is

18. A prostaglandin analog according to claim 17, wherein m is 3.

19. A prostaglandin analog according to claim 18, wherein g is 3.

20. 2-Decarboxy-2-hydroxymethyl-2a,2b-dihomo-15-methyl-13,14-didehydro-16-phenoxy-17,18,19,20-tetranor-$PGF_1\alpha$, a prostaglandin analog according to claim 19.

21. 2-Decarboxy-2-hydroxymethyl-2a,2b-dihomo-13,14-didehydro-16-phenoxy-17,18,19,20-tetranor-$PGF_1\alpha$, a prostaglandin analog according to claim 19.

22. A prostaglandin analog according to claim 18, wherein g is 1.

23. A prostaglandin analog according to claim 22, wherein at least one of $R_3$ and $R_4$ is methyl.

24. A prostaglandin analog according to claim 23, wherein $R_3$ and $R_4$ are both methyl.

25. 2-Decarboxy-2-hydroxymethyl-13,14-didehydro-16-methyl-16-phenoxy-18,19,20-trinor-$PGF_1\alpha$, a prostaglandin analog according to claim 24.

26. A prostaglandin analog according to claim 22, wherein at least two of $R_3$, $R_4$, and $R_5$ are methyl.

27. A prostaglandin analog according to claim 26, wherein $R_3$, $R_4$, and $R_5$ are all methyl.

28. 2-Decarboxy-2-hydroxymethyl-15,16-dimethyl-13,14-didehydro-16-phenoxy-18,19,20-trinor-$PGF_1\alpha$, a prostaglandin analog according to claim 27.

29. A prostaglandin analog according to claim 22, wherein $R_3$ and $R_4$ are both hydrogen.

30. A prostaglandin analog according to claim 29, wherein $R_5$ is methyl.

31. 2-Decarboxy-2-hydroxymethyl-15-methyl-13,14-didehydro-16-phenoxy-17,18,19,20-tetranor-$PGF_1\alpha$, a prostaglandin analog according to claim 30.

32. A prostaglandin analog according to claim 29, wherein $R_5$ is hydrogen.

33. 2-Decarboxy-2-hydroxymethyl-13,14-didehydro-16-phenoxy-17,18,19,20-tetranor-$PGF_1\alpha$, a prostaglandin analog according to claim 32.

34. A prostaglandin analog according to claim 5, wherein $Z_{10}$ is cis—CH=CH—$CH_2$—$(CH_2)_g$—$CH_2$—.

35. A prostaglandin analog according to claim 34, wherein $M_1$ is

36. A prostaglandin analog according to claim 35, wherein m is 3.

37. A prostaglandin analog according to claim 36, wherein g is 3.

38. 2-Decarboxy-2-hydroxymethyl-2a,2b-dihomo-15-epi-13,14-didehydro-16-phenoxy-17,18,19,20-tetranor-$PGF_2\alpha$, a prostaglandin analog according to claim 37.

39. 2-Decarboxy-2-hydroxymethyl-2a,2b-dihomo-15-epi-13,14-didehydro-16-phenoxy-17,18,19,20-tetranor-$PGF_2\alpha$, a prostaglandin analog according to claim 37.

40. A prostaglandin analog according to claim 36, wherein g is 1.

41. A prostaglandin analog according to claim 40, wherein at least one of $R_3$ and $R_4$ is methyl.

42. 2-Decarboxy-2-hydroxymethyl-15-epi-13,14-didehydro-16-methyl-16-phenoxy-18,19,20-trinor-$PGF_2\alpha$, a prostaglandin analog according to claim 41.

43. A prostaglandin analog according to claim 40, wherein at least two of $R_3$, $R_4$, and $R_5$ are methyl.

44. 2-Decarboxy-2-hydroxymethyl-15-epi-15,16-dimethyl-13,14-didehydro-16-phenoxy-18,19,20-trinor-$PGF_2\alpha$, a prostaglandin analog according to claim 43.

45. A prostaglandin analog according to claim 40, wherein $R_3$ and $R_4$ are both hydrogen.

46. 2-Decarboxy-2-hydroxymethyl-15-epi-15-methyl-13,14-didehydro-16-phenoxy-17,18,19,20-tetranor-$PGE_2\alpha$, a prostaglandin analog according to claim 45.

47. A prostaglandin analog according to claim 34, wherein $M_1$ is

48. A prostaglandin analog according to claim 47, wherein m is 3.

49. A prostaglandin analog according to claim 48, wherein g is 3.

50. A prostaglandin analog according to claim 49, wherein at least one of $R_3$ and $R_4$ is methyl.

51. 2-Decarboxy-2-hydroxymethyl-2a,2b-dihomo-16,16-dimethyl-13,14-didehydro-16-phenoxy-17,18,19,20-tetranor-$PGF_2\alpha$, a prostaglandin analog according to claim 50.

52. A prostaglandin analog according to claim 49, wherein at least two of $R_3$, $R_4$, and $R_5$ are methyl.

53. 2-Decarboxy-2-hydroxymethyl-2a,2b-dihomo-15,16-dimethyl-13,14-didehydro-16-phenoxy-18,19,20-trinor-$PGF_2\alpha$, a prostaglandin analog according to claim 52.

54. A prostaglandin analog according to claim 49, wherein $R_3$ and $R_4$ are both hydrogen.

55. 2-Decarboxy-2-hydroxymethyl-2a,2b-dihomo-15-methyl-13,14-didehydro-16-phenoxy-17,18,19,20-tetranor-$PGF_2\alpha$, a prostaglandin analog according to claim 54.

56. A prostaglandin analog according to claim 48, wherein g is 1.

57. A prostaglandin analog according to claim 56, wherein at least one of $R_3$ and $R_4$ is methyl.

58. A prostaglandin analog according to claim 57, wherein only one of $R_3$ and $R_4$ is methyl.

59. 2-Decarboxy-2-hydroxymethyl-13,14-didehydro-16-phenoxy-18,19,20-trinor-PGF$_2\alpha$, a prostaglandin analog according to claim 58.

60. A prostaglandin analog according to claim 57, wherein R$_3$ and R$_4$ are both methyl.

61. 2-Decarboxy-2-hydroxymethyl-13,14-didehydro-16-methyl-16-phenoxy-18,19,20-trinor-PGF$_2\alpha$, a prostaglandin analog according to claim 60.

62. A prostaglandin analog according to claim 56, wherein R$_3$ and R$_4$ are both hydrogen.

63. A prostaglandin analog according to claim 62, wherein R$_5$ is methyl.

64. 2-Decarboxy-2-hydroxymethyl-15-methyl-13,14-didehydro-16-phenoxy-17,18,19,20-tetranor-PGF$_2\alpha$, a prostaglandin analog according to claim 63.

65. A prostaglandin analog according to claim 62, wherein R$_5$ is hydrogen.

66. 2-Decarboxy-2-hydroxymethyl-13,14-didehydro-16-phenoxy-17,18,19,20-tetranor-PGF$_2\alpha$, a prostaglandin analog according to claim 65.

* * * * *

UNITED STATES PATENT OFFICE
CERTIFICATE OF CORRECTION

Patent No. 4,130,591                     Dated 19 December 1978

Inventor(s) Herman W. Smith

It is certified that error appears in the above-identified patent and that said Letters Patent are hereby corrected as shown below:

Column 2, lines 21-23, "with the further proviso that $Z_3$ is oxa only when $R_3$ and $R_4$ are hydrogen or methyl, being the same or different" should be deleted;

Column 4, line 32, "$PGE_2\alpha$" should read -- $PGF_2\alpha$ --.

Signed and Sealed this

Fourth Day of September 1979

[SEAL]

Attest:

LUTRELLE F. PARKER

*Attesting Officer*     *Acting Commissioner of Patents and Trademarks*

UNITED STATES PATENT OFFICE
CERTIFICATE OF CORRECTION

Patent No.  4,130,591    Dated  19 December 1978

Inventor(s)  Herman W. Smith

It is certified that error appears in the above-identified patent and that said Letters Patent are hereby corrected as shown below:

Column 2, line 9, "cis-CH=CH-CH-$(CH_2)_g$-$CH_2$-" should read -- cis-CH=CH-$CH_2$-$(CH_2)_g$-$CH_2$- --;  line 42, "wherein is" should read -- wherein $D$ is --.

Column 3, lines 25-26, delete claim 18; line 27, "according to claim 18" should read -- according to claim 17 --;

Column 4, lines 6-7 and 40-41, delete claims 36 and 48; line 8, "according to claim 36" should read -- according to claim 35 --; line 42, "according to claim 48" should read -- according to claim 47 --.

Signed and Sealed this

Fourteenth Day of October 1980

[SEAL]

Attest:

SIDNEY A. DIAMOND

Attesting Officer    Commissioner of Patents and Trademarks